United States Patent [19]
Siegel

[11] Patent Number: 6,077,252
[45] Date of Patent: Jun. 20, 2000

[54] SINGLE OR MULTIPLE DOSE SYRINGE

[76] Inventor: Robert Siegel, 81 Cedar Ave., Pleasantville, N.Y. 10570

[21] Appl. No.: 08/932,619

[22] Filed: Sep. 17, 1997

[51] Int. Cl.[7] .................................................. A61M 5/178
[52] U.S. Cl. .......................... 604/214; 604/191; 604/204; 604/212; 604/216; 604/232
[58] Field of Search ..................................... 604/191, 181, 604/187, 132, 142, 148, 153, 185, 199, 200, 201–202, 204, 207, 232, 234, 228, 205, 212, 213, 214, 216, 277; 128/DIG. 15

[56] References Cited

U.S. PATENT DOCUMENTS

| | | |
|---|---|---|
| 2,950,717 | 8/1960 | Bouet . |
| 3,115,135 | 12/1963 | Sarnoff ..................................... 604/228 |
| 5,609,580 | 3/1997 | Kwiatkowski et al. ................. 604/216 |
| 5,688,252 | 11/1997 | Matsuda et al. ........................ 604/228 |
| 5,836,922 | 11/1998 | Hansen et al. .......................... 604/214 |

*Primary Examiner*—Ronald K. Stright, Jr.
*Attorney, Agent, or Firm*—Susan P. Petraglia

[57] ABSTRACT

An improved single- or multiple-dose syringe having a conventional housing and an improved plunger configuration carrying a medicament- or saline-filled cartridge the contents of which are sequentially dispensed after the dispensing of a volume of a drawn-up primary fluid. A method for sequential administration of medicinal fluids using the improved syringe is also a part of the invention.

4 Claims, 3 Drawing Sheets

SINGLE OR MULTIPLE DOSE SYRINGE

BACKGROUND OF THE INVENTION

The present invention relates to a multiple dose syringe which sequentially dispenses different fluids from a single housing. U.S. Pat. Nos. 2,950,717; 4,439,184 and 5,102,388 typify this type of syringe, with each being compartmentalized in some fashion to achieve the progressive discharge of the fluids therefrom. U.S. Pat. No. 2,950,717 to Bouet segregates the plural fluids to be administered by placing one of the fluids in a cartridge. Both U.S. Pat. No. 4,439,184 (to Wheeler) and U.S. Pat. No. 5,102,388 (to Richmond) exemplify the partitioning of the syringe to segregate the fluids.

These patents teach that using a single syringe to dispense a plurality of different fluids directly into a patient or into an IV port is economically advantageous and time-saving as compared to using a plurality of the same to accomplish the end result. Additionally, whenever the need arises to administer a plurality of medications or medication and saline flush to a patient, the use of a single syringe greatly reduces the chances of an inadvertent needle-stick injury to the administering party. The background explanations of the latter two patents set forth the problems of the prior art and the advantages of the single-multiple dose syringe, and the same are incorporated here by reference.

The present invention is directed to the general structure of the Bouet patent and is an improvement thereover by the utilization of different, more simplified means to connect the dispensing and collapsing cartridge to the plunger.

SUMMARY OF THE INVENTION

The syringe of the present invention is an improvement over that as disclosed by Bouet in U.S. Pat. No. 2,950,717. As seen in that patent, the cartridge is threaded onto the piston which necessitates additional manufacturing steps. Since both the female receiving portion of the cartridge and the male connecting portion of the piston have to be threaded this increases the cost of manufacture and assembly time. The present invention distinguishes over designs such as in Bouet inasmuch as in one embodiment herein the cartridge is formed with a collar which easily engages the plunger for attachment thereto, and is also easily and quickly removed therefrom once the cartridge contents have been dispensed. Alternatively, the present invention includes the use of other suitable releasing fasteners, hook-and-loop type fasteners, a releasable adhesive or other complimentary engagement means, as further embodiments of the improvement herein.

DESCRIPTION OF THE PREFERRED EMBODIMENT

Figure 1:
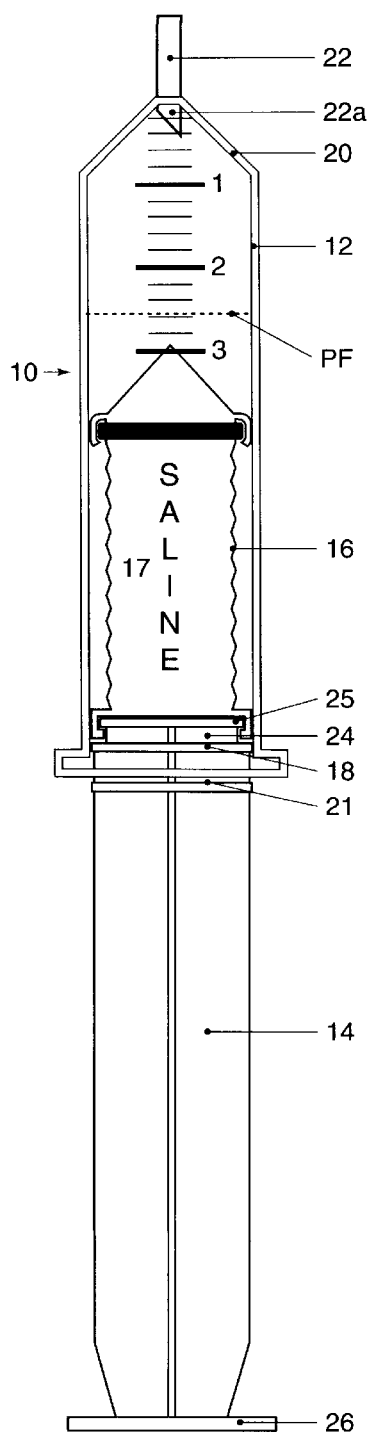
FIG. 1 is a view of the syringe showing the various components of the same.

With reference to FIG. 1, the syringe of the present invention is shown generally at 10 and is seen to comprise a housing 12, a plunger 14 disposed therein, and a collapsible cartridge 16, having a charge of fluid 17, removably secured to the plunger 14 at plunger end 18. The housing 12 is of a conventional elongated cylindrical shape having a tapered dispensing end 20 with a syringe tip 22 disposed in the dispensing end 20, and a plunger 14 receiving aperture 21 at the opposite end thereof. Syringe tip 22 has a piercing end 22a extending into the dispensing end of the housing 12 in order to pierce the cartridge 16 for dispensing the fluid charge 17 therefrom in known fashion. The housing 12 optionally has graduated indicia 11 etched, inscribed or otherwise disposed thereon to facilitate the measurement, or drawing up, of a volume of a primary fluid PF. The plunger 14 which is of a complementary shape to the interior of the housing 12 is an elongated rod having a plunger end 18 and a handle 26 at the opposite end thereof for manipulating the plunger once it is fitted in the syringe housing. The plunger end 18 contains a cartridge-engaging portion 24 formed with a collar 25.

Figure 2:
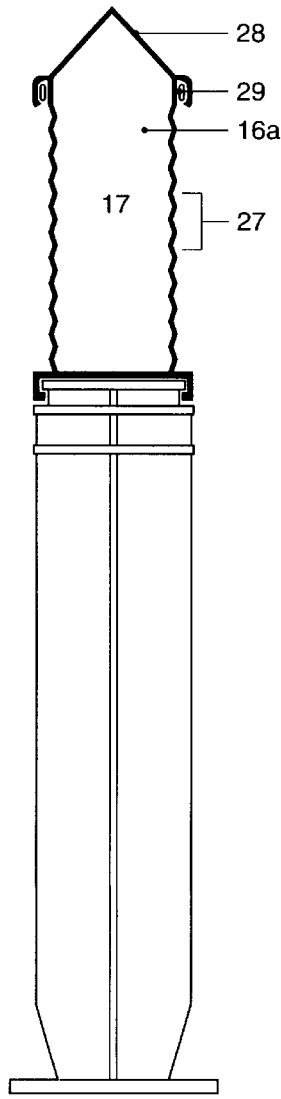
FIG. 2 is a view of the plunger and cartridge.
Figure 3:
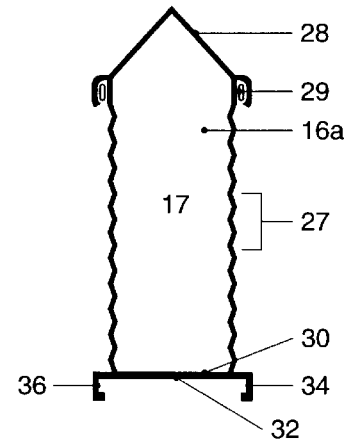
FIG. 3 is a cross-sectional view of the cartridge.
Figure 6:
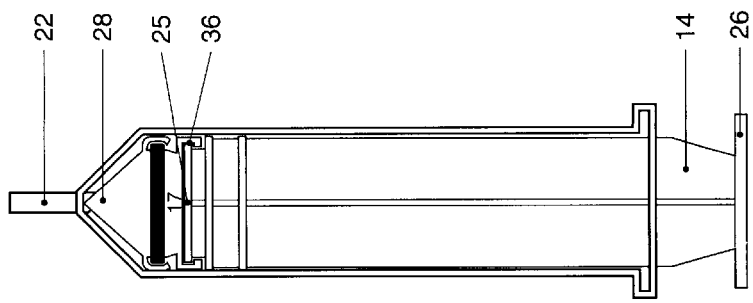
FIGS. 4–6 show the sequential delivery of plural fluids from the syringe according to the invention.

With reference to FIGS. 2 and 3, the cartridge 16 has a generally cylindrical body 16a having a bellows-type collapsing feature 27. Cartridge 16 further has a tapered end 28 complimentary to the shape of the internal walls of the dispensing end 20 of housing 12. In this fashion, cartridge end 28 will seat against the internal walls of the dispensing end 20 to ensure the complete dispensing of the fluid charge 17 therefrom. Although not an essential feature, a ring 29, or other reinforcement means such as thickened plastic or a rubber gasket, can be secured via suitable securing means to the forward-most portion of the cylindrical body 16a of cartridge 16 at the juncture of cylindrical body 16a and tapered end 28. Ring 29, when present, strengthens the dispensing end to absorb forces when the cartridge body 16a is collapsing during the dispensing of the fluid charge contained therein. The ring also prevents the primary fluid and the fluid charge 17 being dispensed from the cartridge from seeping into the void volume V (shown in FIG. 4) formed between the internal wall of housing 12 and the collapsing cartridge 16, thereby ensuring complete delivery of the measured plural fluids within high confidence limits. The plunger-engaging end 30 of the cartridge body 16a is sealed by a top or a cap 32 having a collar 34 with an in-turned flange 36 for removably securing the same to the cartridge-engaging portion 24 of plunger end 18. The cartridge is charged with fluid in a known fashion and as such does not constitute a part of the present invention.

The housing 12 and plunger 14 are formed from customary materials recognized in the syringe art, for example, glass or thermoplastic materials, and more preferably, are injection-molded or by other suitable technique molded from hard plastic. The cartridge is formed from durable, fluid-impermeable, soft plastic which can be readily collapsed when forced against the housing dispensing end 20 under the action of plunger end 18. The cartridge material can be formed of a single sheet material or a laminate material so long as it conforms to the above-stated requirements. Techniques for preparing a collapsing bellows-type container are well-known in the container art and as such do not form a part of the invention.

Figure 5:
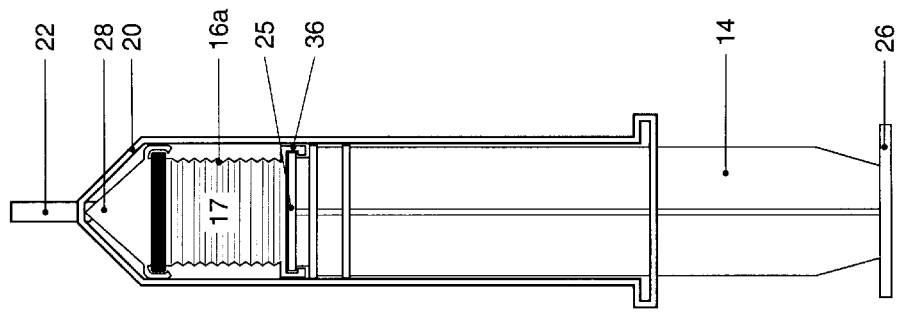
Figure 4:
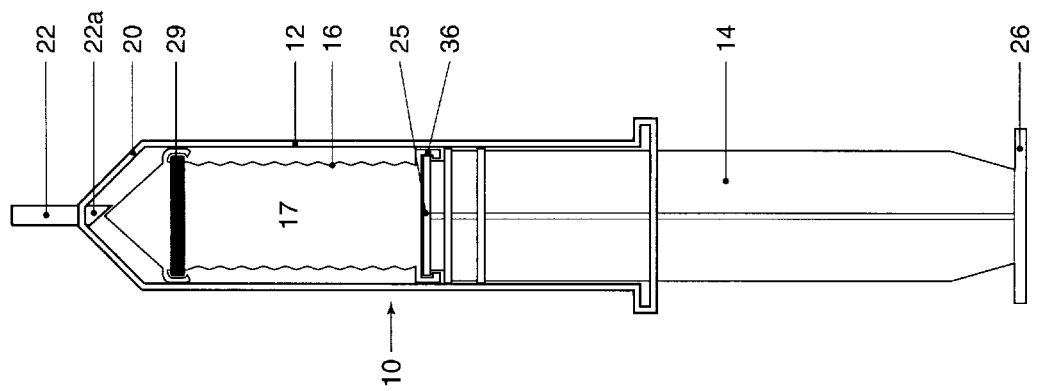

To use the syringe 10, the cartridge 16, which is removably secured to the plunger 14 by engagement of the in-turned flange 36 to the plunger collar 25, is positioned in the housing 12 as shown in FIG. 1. The plunger-cartridge assembly is then retracted to draw up a volume of primary fluid into the internal space of housing 12. Graduated indicia 11 are provided on the housing to facilitate measurement of the volume of primary fluid to be dispensed first. It is to be understood that any air bubbles in the drawn-up volume of primary fluid are expelled before the primary fluid is dispensed. Next the plunger 14 is pushed further into housing 12, forcing the primary fluid through the syringe tip 22 to the point as seen in FIG. 4 wherein the tapered end 28 of the cartridge 16 is pierced by engaging with the piercing end 22a of syringe tip 22. Bellows 27 begin to collapse in response to the continual force placed on the plunger 14 as seen in FIG. 5 to start the dispensing of the fluid 17 therefrom. This procedure continues until the bellows 27 are totally collapsed and seated against dispensing end 20 to ensure and complete the discharge of the fluid charge 17. The plunger 14 and cartridge 16 are then withdrawn from the housing 12, and the used cartridge removed from the plunger end and discarded.

The drawings of the present invention show saline as being the fluid charge 17 in the cartridge 16. In this instance, the syringe is used to deliver plural fluids, first delivering a measured dose of a medicament (as a primary fluid), followed by dispensing of the saline as a flush to push the primary fluid through, or further along, the IV line or into the vein of the recipient, as is well known. However, it is also within the present embodiments that the syringe be used to deliver a single fluid. In this scenario, the cartridge 16 contains, for example, a pre-measured sterile dose of a medicament, and the syringe housing 12 can be devoid of volume indicia.

Figure 8:
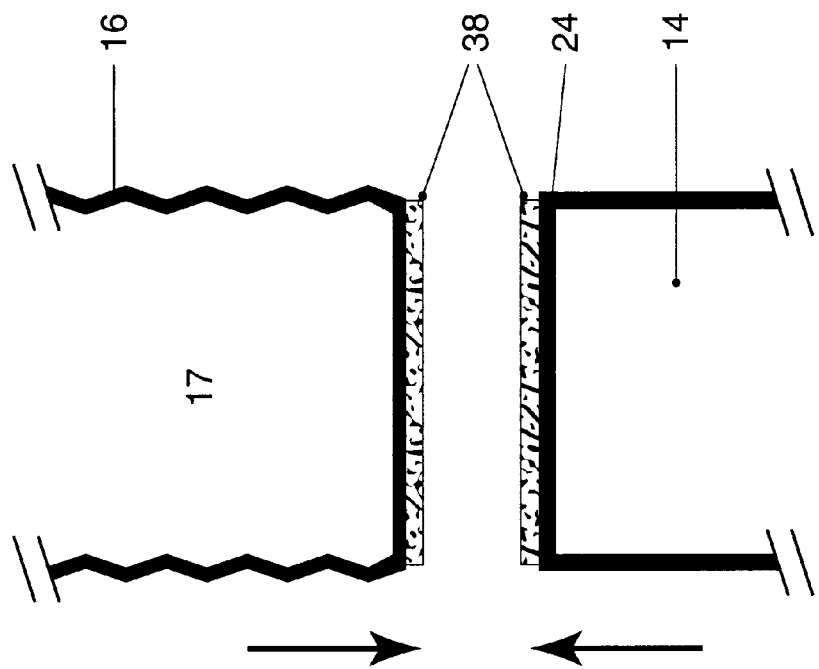
FIGS. 7 and 8 depict alternative connecting means for the engaging ends of the plunger and the cartridge.
Figure 7:
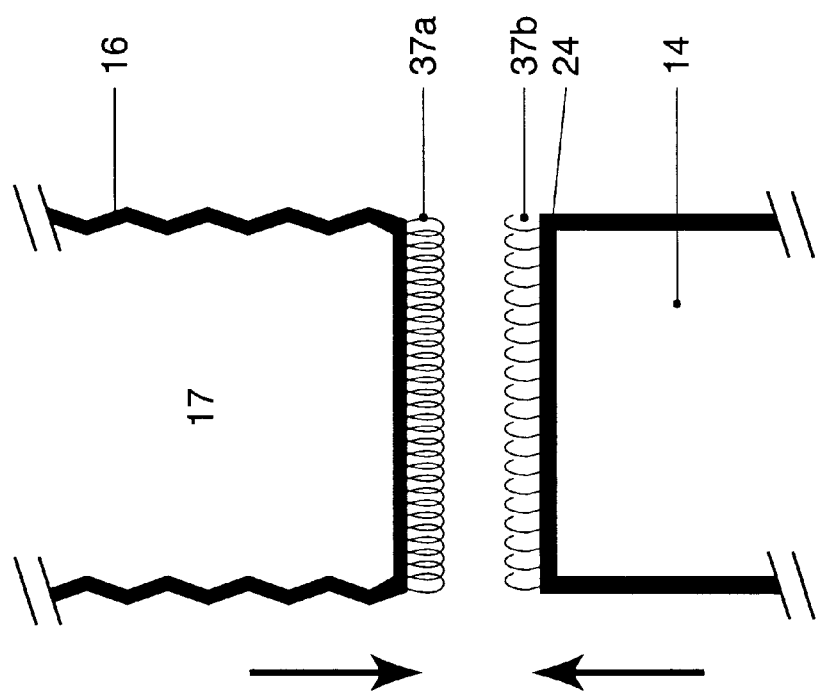

It is considered to be within the scope of the present invention to use a hook-and-loop fastener (such as, e.g., Velcro®) 37a and 37b as shown in FIG. 7, releasably secured or low-grade adhesive 38 as shown in FIG. 8, or any other known releasable fasteners in lieu of the connecting means 25 and 36 disclosed hereinabove for securing the cartridge 16 to the plunger 14.

In one embodiment, the free end (not shown) of syringe tip 22 is blunt-ended, which facilitates introduction of the syringe tip into an IV port. Alternatively, the free end of syringe tip 22 may also be a pointed, piercing end similar to the opposite end 22a to permit usage of the syringe in a vein of the patient (as shown at 10 in the Bouet U.S. Pat. No. 2,950,717). When the invention is embodied with a syringe tip having a blunt free end, it is also intended that the syringe tip be capable of receiving a detachable needle (not shown). Attachment of the needle permits the user to measure a specific volume of a primary fluid from a container requiring piercing (e.g., a vial with a septum), followed by removal of the same to expose the blunt end of the tip for insertion into an IV port.

The description of the foregoing embodiments of the invention pertain to the syringe apparatus. However, the invention also includes the method of using the syringe to sequentially administer plural fluids, one of which (typically a therapeutic agent) is measured or drawn up, and the other of which is a volume contained in the cartridge, preferably a saline flush. Thus a method of administering plural volumes of diverse fluids from a single syringe having a housing with graduated volume indicia thereon, a plunger assembly that includes a plunger and a fluid-filled collapsible cartridge attached thereto, and cartridge-piercing means, includes the following steps: 1) Measuring a specific volume of a primary fluid into the syringe by withdrawing the plunger assembly which is partially seated in the syringe housing. 2) Expelling air bubbles in the measured volume of primary fluid by pushing the plunger assembly slightly forward to force the air out the syringe tip. 3) Dispensing the volume of primary fluid either directly or indirectly into a patient by advancing the plunger assembly in the syringe housing and displacing the primary fluid through the syringe tip, and 4) dispensing the fluid contained in the collapsible cartridge by piercing engagement of the foremost advancing wall of the cartridge with the cartridge piercing means and collapsing the cartridge by continued forward advancement of the plunger until it is completely seated in the syringe housing.

The present invention may be embodied in other specific forms without departing from its spirit or essential characteristics and the above-described materials are to be considered to be illustrative rather than restrictive. The scope of the invention is, therefore, indicated by the appended claims rather than by the foregoing description. All changes which come within the meaning and range of equivalency of the claims are to be embraced within their scope.

What is claimed is:

1. A syringe for dispensing plural fluids including a housing having an open end and a dispensing end, a plunger slidably disposed therein, said plunger having a plunger end thereof disposed within said housing and having nonthreadable releasable securing means, a collapsible cartridge having a dose of a fluid therein, said cartridge having nonthreadable releasable securing means complementary to said nonthreadable releasable securing means of said plunger end for securing the cartridge to said plunger end to be moved thereby, and piercing means at the dispensing end of said housing for puncturing said cartridge upon engagement therewith for dispensing said dose of fluid in said collapsible cartridge through said dispensing end, wherein said nonthreadable releasable securing means of said plunger end and cartridge comprise a hook-and-loop fastener.

2. The syringe of claim 1 further comprising a reinforcing ring disposed around said collapsible cartridge at a forwardly-advancing end thereof.

3. A syringe for dispensing plural fluids including a housing having an open end and a dispensing end, a plunger slidably disposed therein, said plunger having a plunger end thereof disposed within said housing and having nonthreadable releasable securing means, a collapsible cartridge having a dose of a fluid therein, said cartridge having nonthreadable releasable securing means complementary to said nonthreadable releasable securing means of said plunger end for securing the cartridge to said plunger end to be moved thereby, and piercing means at the dispensing end of said housing for puncturing said cartridge upon engagement therewith for dispensing said dose of fluid in said collapsible cartridge through said dispensing end, wherein said nonthreadable releasable securing means of said plunger end and cartridge comprise a releasable or low-grade adhesive.

4. The syringe of claim 3 further comprising a reinforcing ring disposed around said collapsible cartridge at a forwardly-advancing end thereof.

\* \* \* \* \*